US008425778B2

(12) United States Patent
Liu et al.

(10) Patent No.: US 8,425,778 B2
(45) Date of Patent: Apr. 23, 2013

(54) ORGANOSILANES AND SUBSTRATE BONDED WITH SAME

(75) Inventors: Xiadong Liu, Cupertino, CA (US); Christopher A. Pohl, Union City, CA (US); Andrei V. Bordunov, Campbell, CA (US); Nebojsa Avdalovic, Cupertino, CA (US)

(73) Assignee: Dionex Corporation, Sunnyvale, CA (US)

( * ) Notice: Subject to any disclaimer, the term of this patent is extended or adjusted under 35 U.S.C. 154(b) by 0 days.

(21) Appl. No.: 13/464,644

(22) Filed: May 4, 2012

(65) Prior Publication Data

US 2013/0026099 A1 Jan. 31, 2013

Related U.S. Application Data

(62) Division of application No. 12/111,059, filed on Apr. 28, 2008, now Pat. No. 8,182,679, which is a division of application No. 10/938,172, filed on Sep. 10, 2004, now Pat. No. 7,402,243.

(51) Int. Cl.
*B01D 15/08* (2006.01)

(52) U.S. Cl.
USPC ...... 210/635; 210/198.2; 210/656; 210/502.1

(58) Field of Classification Search .......... 210/635, 210/656, 658, 659, 198.2, 502.1; 502/401
See application file for complete search history.

(56) References Cited

U.S. PATENT DOCUMENTS

| | | | |
|---|---|---|---|
| 3,660,454 A | 5/1972 | Gornowicz et al. |
| 4,061,828 A | 12/1977 | Mazarguil et al. |
| 4,177,038 A | 12/1979 | Biebricher et al. |
| 4,213,860 A | 7/1980 | Tsibris |
| 4,322,310 A | 3/1982 | House |
| 4,415,631 A | 11/1983 | Schutijser |
| 4,431,546 A | 2/1984 | Hughes et al. |
| 4,627,919 A | 12/1986 | Yuki |
| 4,650,784 A | 3/1987 | Ramsden et al. |
| 4,773,994 A | 9/1988 | Williams |
| 4,778,600 A | 10/1988 | Williams |
| 4,778,909 A | 10/1988 | Karger et al. |
| 4,830,921 A | 5/1989 | Kitayama et al. |
| 4,837,348 A | 6/1989 | Stolowitz et al. |
| 4,883,598 A | 11/1989 | Riethorst et al. |

(Continued)

FOREIGN PATENT DOCUMENTS

| DE | 22 41 014 A1 | 3/1973 |
|---|---|---|
| DE | 3223101 C2 | 6/1987 |

(Continued)

OTHER PUBLICATIONS

Alpert, AJ. Hydrophilic-interaction chromatography for the separation of peptides, nucleic acids and other polar compounds, *J. Chromatogr.* 499:177-1196 (1990).

(Continued)

*Primary Examiner* — Ernest G Therkorn
(74) *Attorney, Agent, or Firm* — Richard Trecartin

(57) ABSTRACT

The present invention provides novel silicon compounds, methods for making these novel silicon compounds, compositions comprising these novel silicon compounds attached to substrates, methods for attaching the novel silicon compounds to substrates and methods for using the compositions in a variety of chromatographic applications.

3 Claims, 3 Drawing Sheets

Peak 1 is α-Methylbenzylamine
Peak 2 is Toluene
Peak 3 is Fumaric acid
Peak 4 is p-Butylbenzoic acid

U.S. PATENT DOCUMENTS

| | | | |
|---|---|---|---|
| 4,985,144 | A | 1/1991 | Quentin-Millet et al. |
| 4,997,965 | A | 3/1991 | Lohmann et al. |
| 5,043,062 | A | 8/1991 | Bale et al. |
| 5,045,190 | A | 9/1991 | Carbonell et al. |
| 5,103,000 | A | 4/1992 | Akiyama et al. |
| 5,135,649 | A | 8/1992 | Kanda et al. |
| 5,137,627 | A | 8/1992 | Feibush |
| 5,149,426 | A | 9/1992 | Watabe et al. |
| 5,240,602 | A | 8/1993 | Hammen |
| 5,277,813 | A | 1/1994 | Feibush et al. |
| 5,318,848 | A | 6/1994 | Itoh et al. |
| 5,374,755 | A | 12/1994 | Neue et al. |
| 5,843,312 | A | 12/1998 | Manz et al. |
| 5,868,938 | A | 2/1999 | Bömer et al. |
| 5,945,520 | A | 8/1999 | Burton et al. |
| 6,020,448 | A | 2/2000 | Jenkner et al. |
| 6,310,199 | B1 | 10/2001 | Smith et al. |
| 6,375,846 | B1 | 4/2002 | Jarrett |
| 6,645,378 | B1 | 11/2003 | Liu et al. |
| 6,949,186 | B2 | 9/2005 | Liu et al. |
| 7,074,491 | B2 | 7/2006 | Liu et al. |
| 7,402,243 | B2 | 7/2008 | Liu et al. |
| 7,906,670 | B2 | 3/2011 | Toujo et al. |
| 8,182,679 | B2 * | 5/2012 | Liu et al. .............. 210/198.2 |
| 2003/0196958 | A1 | 10/2003 | Liu et al. |
| 2003/0215801 | A1 | 11/2003 | Pieken et al. |
| 2005/0178730 | A1 | 8/2005 | Li |
| 2006/0054559 | A1 | 3/2006 | Liu et al. |
| 2006/0180549 | A1 | 8/2006 | Liu et al. |

FOREIGN PATENT DOCUMENTS

| | | |
|---|---|---|
| EP | 0885895 A2 | 5/1998 |
| EP | 0885895 A3 | 5/1998 |
| EP | 1 110 967 A1 | 6/2001 |
| EP | 1 205 177 A2 | 5/2002 |
| GB | 882059 | 11/1961 |
| GB | 2074892 A | 11/1981 |
| JP | 56027648 A2 | 3/1981 |
| WO | WO 86/06072 A1 | 10/1986 |
| WO | WO 02/088222 A1 | 11/2002 |
| WO | WO 2006/013060 A1 | 2/2006 |

OTHER PUBLICATIONS

Annis, D., et al., "Polymer-supported chiral Co(salen) complexes," *J. Am. Chem. Soc.* 121(17):4147-4154 (1999).

Anon., "Novel Stationary Phases," *from SIELC website* (last accessed Jun. 21, 2004), located at <http://allsep.com/Technology_NovelStationaryPhases.php>.

Berendsen et al., "Role of Chain Length of Chemically Bonded Phased and the Retention Mechanis in reversed-Phas Liquid Chromatography," *Journal of Chromatography*, 1980, 196, 21-37.

Bischoff, R., et al., "Chemically synthesized hydrophobic anion-exchange high-performance liquid chromatography supports used for oligonucleotide resolution by mixed mode chromatography," *J. Chromatogr. A* 270:117-126 (1983).

Bischoff, R., et al., "Nucleic acid resolution by mixed-mode chromatography," *J. Chromatogr. A* 296:329-337 (Jul. 1984).

Galas, R. A trimethoxyslyloamine and a trimethoxysilyl ketone derived from 10-undecenoic acid, Rev. Frac. Corps Gras 3:5-9 (1956).

Database Beilstein [Online] Beilstein Institute for Organic Chemistry, Frankfurt-Main, DE; 2000, Database accession No. BRN 10507664.

Gershevitz et al.: "Interfacial Chemistry on Carboxylatefunctionalized Monolayer Assemblies" Israel Journal of Chemistry, vol. 45, No. 3, Jun. 30, 2005, pp. 321-336.

Gershevitz, et al. http://www.sciencefromisrael.com/app/home/contibution.asp?referrer=parent&backt . . . .

McDonald et al., Solid Phase Extraction Applications: Guide and Bibliography, A Resource Guide for Sample Preparation Methods Development, Method Development Manual and Comprehensive Compendium of World wide Waters Sep-Pack Cartridge, 1995, 6th Edition, pp. 23. Milford, Massachusetts.

Moreau, Joel J.E., Benoit P. Pichon, Guilhem Arrachart, Michel Wong Chi Man and Catherine Bied:"Nanostructuring organo-silicas: combination of intermolecular interactions and molecular recognition properties to generate self-assembled hybrids with phenylene or adeninethymine bridging units." New Journal of Chemistry, vol. 29, Mar. 31, 2005,pp. 653-658.

Neue, "HPLC Columns: Theory, Technology, and Practice," John Wiley & Sons, 1997,New York, NY.

Neue, U. Hydrophilic-interaction chromatography, HPLC Columns—Theory, Technology and Practice:217-223, Wiley-Vch, NY (1997).

Neue, U. Normal-phase chromatography, HPLC Columns—Theory, Technology and Practice:164-181), Wiley-Vch, NY (1997).

Neue, U., *HPLC Columns: Theory, Technology and Practice*, pp. 183-249, John Wiley & Sons, Ltd.: New York, NY (Jul. 1997).

Nimura, N., Hiroko, I., Kinoshita, T. Diol-bonded silica gel as a restricted access packing forming a binary-layered phase for direct injection of serum for the determination of drugs, *J. Chromatog. A* 689:203-210 (1995).

O'Gara, J., et al., "Embedded-polar-group bonded phases for high performance liquid chromatography," *LC-GC* 19(6):632-641 (Jun. 2001).

Olsen,BA. Hydrophilic interaction chromatography using amino and silica columns for the determination of polar pharmaceuticals and impurities, *J. Chromatogr. A* 913:113-122 (2001).

Oviatt, H., et al., "Applications of organic bridged polysilsequioxane xerogels to nonlinear optical materials by the Sol-Gel method," *Chem. Mat.* 7(3):493-498 (Mar. 1995).

Pesek, J.J., Matyska, M.T. Synthesis and spectrometric characterization of a true diol bonded phase, *J. Chromatog. A* 687:33-44 (1994).

Pirkle, William H., Thomas C. Pochapsky, George S. Mahler, Debbi E. Corey, Daniel S. Reno, Donna M. Alessi: "Useful and easily prepared chiral stationary phases for the direct chromatographic separation of the enantiomers of a variety of derivatized amines, amino acids, alcohols, and related compounds" J. Org. Chem, vol. 51, No. 25, 1986, pp. 4991-5000.

Schmitt, T. Analysis of surfactants, 2d ed., pp. 197-292, Marcel Dekker, Inc., New York, NY (2001).

Seibert, D.S., Poole, C.F., Abraham, M.H. Retention properties of a spacer-bonded propanediol sorbent for reversed-phase liquid chromatography and solid-phase extraction, *Analyst* 121:511-520 (Apr. 1996).

SeQuant. Hydrophilic stationary phase for liquid chromatography, sequant.com (products).

(Abstract of) Silicon-containing amides. IV. Reaction to sodium ethylecetamide with methyldialkoxychloromethylsilanes, Zhurnal Obshchei Khimii (USSR) 38(11):2582-2585 (1968).

Snyder, Introduction to Modern Liquid Chromatography, pp. 272-275, John Wiley 1979.

Speier, J. et al. Synthesis of (3-aminoalkyl) silcon compounds, J. Org. Chem. 36(21):3120-3126 (1971.

Tanaka, H, X Zhou et al. Characterization of a novel diol column for high-performance liquid chromatography, *J. Chromatogr. A* 987:119-125 (2003).

Prado, A.G.S. et al. Adsorption and separation of cations on silica gel chemicall modified by homogeneous and heterogeneous routes with the ethylenimine anchored on thiol modified silica gel, *Green Chemistry* 4:42-46 (2002).

Jinno, K. et al. Retention behaviour of polycyclic aromatic hydrocarbons on a liquid-crystal bonded phase in reversed-phase liquid chromatography, *J. Chromatogr.* 557:459-468 (1991).

Kallury, K.M.R. et al. Silanization of oxidized silicon and aluminum surfaces with functinoalized silanes with characterization by wettability, ellipsometry, XPS and quartz crystal microbalance studies, *Colloids and Surfaces* 63:1-9 (1992.

Lochmüller, C.H. Chemically-bonded, charge transfer acceptors for high-performance liquid chromatography, *Silylated Surfaces*, D.E. Leyden and W.T. Collins, eds., Gordon and Breach Science Publishers (Midland Macromolecular Monographs), 231-67 (1980).

Barness, Y. et al. Functionalized silanes for the preparation of siloxane-anchored monoloayers, Langmuir 16:247-251 (2000).

* cited by examiner

Peak 1 is Quinic acid
Peak 2 is Shikimic acid
Peak 3 is Glycolic acid
Peak 4 is Lactic acid
Peak 5 is Acetic acid
Peak 6 is Formic acid
Peak 7 is Ascorbic acid
Peak 8 is Isoascorbic acid
Peak 9 is Propionic acid
Peak 10 is Pyruvic acid
Peak 11 is impurity

ORGANOSILANES AND SUBSTRATE BONDED WITH SAME

1. CROSS-REFERENCES TO RELATED APPLICATIONS

This application is a divisional application of U.S. patent application Ser. No. 12/111,059, filed Apr. 28, 2008, now U.S. Pat. No. 8,182,679, which is a divisional application of U.S. patent application Ser. No. 10/938,172, filed Sep. 10, 2004, now U.S. Pat. No. 7,402,243, the disclosure of which is incorporated herein by reference in its entirety for all purposes.

2. FIELD

The present invention relates generally to novel silicon compounds, methods for making these novel silicon compounds, compositions comprising these novel silicon compounds attached to substrates, methods for attaching the novel silicon compounds to substrates and methods for using the compositions in a variety of chromatographic applications.

3. BACKGROUND

Conventional reversed phase silica columns (e.g., ODS) are widely used as general-purpose stationary phases for chromatographic separations (Neue, "HPLC Columns—Theory, Technology, and Practice," WILEY-VCR, New York, 1997, 183-203). However, some drawbacks, including, for example, "phase collapse" (i.e., dewetting) in highly aqueous environments, weak retention of ionic compounds and residual silanol activity which leads to peak tailing of basic analytes prevent employment of convention reverse phase silica columns in certain applications.

Polar-embedded phases improve the peak shape of basic analytes and enable operation of reverse phase HPLC columns in highly aqueous environments (O'Gara et al., *LC-GC* 2001, 19 (6)632-641). Polar embedded phases are primarily hydrophobic but have hydrophilic groups near the substrate surface. Commonly used polar groups include, for example, amides, ureas, ethers and carbamates. In general, polar-embedded phases provide superior peak shapes of basic analytes and are more compatible with highly aqueous environments when compared to general purpose reverse phases. Further, polar embedded phases often have selectivities which are substantially different from those exhibited by conventional C-18 packings. However, ionic compounds such as small hydrophilic organic acids or inorganic ions are poorly separated, if at all, by chromatography on polar embedded phases.

Typically, ion-exchange chromatography is used to separate ionic or ionizable compounds such as proteins, nucleic acids, inorganic ions, small organic acids, etc. (Neue, supra, 224-249). However, since hydrophobic molecules are poorly retained on most ion exchange resins, ion-exchange chromatography is rarely used in conventional HPLC for the separation of organic molecules.

Ion-pairing chromatography is another method for separating ionic or ionizable compounds (Neue, supra, 209-211). Here, hydrophobic ionic compounds, typically comprised of an alkyl chain with an ionizable terminus, are added to the mobile phase while the stationary phase is conventional reversed-phase medium. Generally, retention of neutral analytes is nearly unaffected, while analytes with charges complementary to the ion-pairing reagent are retained for a longer period of time and analytes with the same charge as the ion-pairing reagent are retained for a shorter period of time. As is known to the skilled artisan, retention of charged analytes may be affected by a variety of factors including, for example, the type and concentration of the ion-pairing reagent, ionic strength and the pH of the mobile phase. Limitations of ion-pairing chromatography include long column equilibration times and the quantity of solvent and time needed to elute the ion-pairing reagent from the column. Further, the presence of ion-pairing reagent complicates the composition of the mobile phase and can interfere with many detection methods, such as, for example, electrochemical detection modes.

Yet another method for separating ionic or ionizable compounds is mixed-mode chromatography, which combines aspects of ion-exchange chromatography and conventional reverse phase chromatography. For example, commercially available aminopropylsilyl bonded phase, modified with different hydrophobic organic acids to provide weakly hydrophobic anion-exchange supports, has been used to separate oligonucleotides (Bischoff et al., *Journal of Chromatography* 1983, 270:117-126). Here, ion-exchange is the primary mode of separation because the hydrophobicity of this resin is due to a three-carbon linker.

Other mixed-mode supports for liquid chromatography which were used to separate nucleic acids have been made by functionalizing anion-exchange surfaces with hydrophobic groups (Bischoff et al, *Journal of Chromatography* 1984, 296:329-337). Although this method can be used to modulate the hydrophobicity of the stationary phase, the slightly different amounts of ion-exchange and hydrophobic sites introduced onto the surface during each functionalization negatively affect support reproducibility. Mixed-mode polymeric resins useful for separating proteins and peptides have been prepared by activation of hydroxylated polymer surfaces with carbonyldiimidazole or epichlorohydrin, followed by reaction with primary amines containing ion-exchange functionality (Burton et al., U.S. Pat. No. 5,945,520). Ion-exchange matrices based on porous magnetic silica particles have used to separate nucleic acids, such as plasmid DNA, chromosomal DNA or RNA from contaminants including proteins, lipids, cellular debris, etc. (Smith et al., U.S. Pat. No. 6,310, 199). Finally, a family of mixed-mode HPLC columns, which have ion-exchange functionality embedded between the silica surface and an alkyl chain and thus provide both ion-exchange and hydrophobic retaining sites have become commercially available (SIELC Technologies, Prospect Heights, Ill.).

Despite the advances in mixed-mode chromatography, supra, novel silane compounds which have both hydrophobic and ionic functionality, substrates functionalized with these new slime compounds and the use of these novel functionalized substrates in mixed mode chromatography are needed to provide for controlled retention of both ionizable and neutral compounds. Ideally, the novel functionalized substrates will retain ionic or ionizable compounds in the absence of ion-pairing reagents, allow for simultaneous analysis and separation of inorganic ions and organic compounds, mask the effect of ion-exchange groups on the residual interaction of basic analytes with surface silanols and increase resistance of developed stationary phases to dewetting in 100% aqueous media.

4. SUMMARY

The present invention satisfies these and other needs by providing a new class of silane compounds, which have hydrophobic and ionic functionality, substrates functionalized with these new slime compounds and the use of these novel functionalized substrates in mixed-mode chromatography.

In one aspect, a compound described by Formula (I) is disclosed:

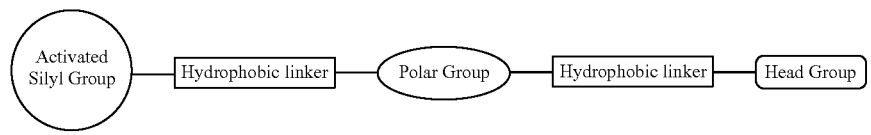

(I)

or salts, solvates or hydrates thereof. The compound of Formula (I) has at least one activated silyl group (e.g., Si(OMe)$_3$, —SiMe(OMe)$_2$, —SiMe$_2$(OMe), —Si(OEt)$_3$, —SiMe(OEt)$_2$, —SiMe$_2$(OEt), —SiMe$_2$NMe$_2$, —SiCl$_3$, etc.) and at least one head group (e.g., amines, phenols and esters thereof, carboxylic acids and esters thereof; sulfonic acids and esters thereof, phosphonic acids and esters thereof, etc.) and at least one polar group (e.g., amide, sulfonamide, carbamate, urea, ester, ether, thioether, etc.) between the activated silyl group and the head group. The head group contains one or more ion-exchange functionalities or groups that can be converted to ion-exchange functionalities. Compounds of Formula (I) also contain two alkyl, aryl, heteroalkyl or heteroaryl linkers, which connect the activated silyl group with the polar group and the polar group with a head group as illustrated, supra.

In some embodiments, compounds of Formula (I) are described by Formula (II):

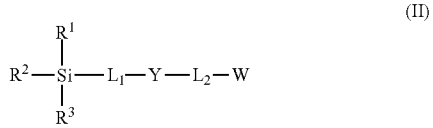

(II)

or salts, solvates or hydrates thereof
wherein:

$R^1$, $R^2$ and $R^3$ are independently alkyl, alkoxy, alkoxycarbonyl, alkylsulfonyloxy, amino optionally substituted with one or more of the same or different $R^{12}$ groups, aryl, aryloxycarbonyl, aryloxy, arylsulfonyloxy, halo or hydroxyl provided that at least one of $R^1$, $R^2$ and $R^3$ are not alkyl, aryl or hydroxyl;

$L_1$ and $L_2$ are independently alkyldiyl, heteroalkyldiyl, aryldiyl or heteroaryldiyl;

Y is —S—, —C(O)N($R^4$)—, —N($R^4$)C(O)—, —N($R^4$)S(O)$_2$—, —S(O)$_2$N($R_4$)—, C(O)O—, —OC(O)—, —OC(O)N($R^4$)—, —N($R^4$)C(O)O—, —N($R^4$)C(O)N($R^5$)— or N($R^4$)C(S)N($R^5$)—;

$R^4$ and $R^5$ are independently hydrogen, alkyl, substituted alkyl, aryl or substituted aryl;

W is —(Z)$_n$OH, —(Z)$_n$N($R^6$)($R^7$), —(Z)$_n$N$^+$($R^6$)($R^7$)($R^8$) X$^-$—, —(Z)$_n$CO$_2$R$^9$, —(Z)$_n$SO$_3$R$^9$, or —(Z)$_n$OP(O)(OR$^9$)(OR$^{10}$) or —(Z)$_n$B(OR$^9$)(OR$^{10}$)(OR$^{11}$), $R^6$, $R^7$ and $R^8$ are independently hydrogen, alkyl or substituted alkyl;

$R^9$, $R^{10}$ and $R^{11}$ are independently hydrogen, alkyl, substituted alkyl, aryl or substituted aryl;

$R^{12}$ is hydrogen or alkyl;

X$^-$ is an anionic counterion;

Z is aryl or substituted aryl; and n is 0 or 1 provided that when W is —(Z)$_n$OH, n is 1.

In another aspect, a composition including a compound of Formula (II) covalently bonded to a substrate is provided. In some embodiments, the composition is in a flow-through bed suitable for use a reverse phase chromatographic medium.

In still another aspect, a chromatographic method is provided. An aqueous liquid is flowed through a bed of separation medium, which includes a composition containing a compound of Formula (II) covalently bonded to a substrate.

In still another aspect, a method for chromatographic separation of analytes in a liquid sample is provided. The liquid sample is flowed through medium, which includes a composition containing a compound of Formula (II) covalently bonded to a substrate.

In still another aspect, a method for simultaneous analysis of inorganic analytes and organic analytes in a liquid sample is provided. The liquid sample is flowed through medium, which includes a composition containing a compound of Formula (II) covalently bonded to a substrate.

5. BRIEF DESCRIPTION OF THE DRAWINGS

6. DETAILED DESCRIPTION

6.1 Definitions

Figure 1:
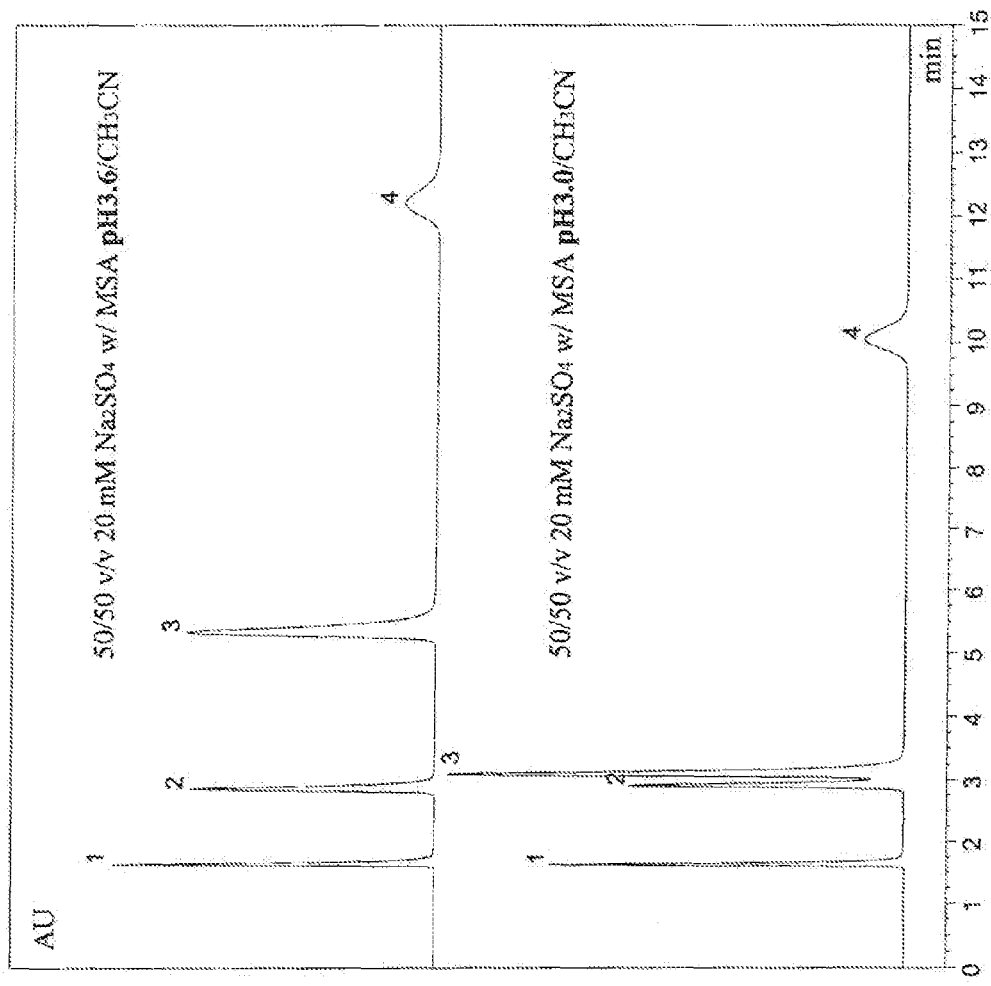
FIG. 1 illustrates the mixed mode character of functionalized support 23.

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-2-yl, prop-2-en-1-yl cycloprop-1-cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, 2-methyl-prop-1-en-1-yl, but-2-en-1-yl, but-2-en-2-yl, buta-1,3-but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 40 carbon atoms. In other embodiments, an alkyl group comprises from 1 to 30 carbon atoms. In still other embodiments, an alkyl group comprises from 1 to 20 carbon atoms. In still other embodiments, an alkyl group comprises from 1 to 10 carbon atoms.

"Alkanyl" by itself or as part of another substituent, refers to a saturated branched, straight-chain or cyclic alkyl radical derived by the removal of one hydrogen atom from a single carbon atom of a parent alkane. Typical alkanyl groups include, hut are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl" by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl, cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent, refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent, refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Preferably, the alkyldiyl group is $(C_1-C_{20})$ alkyldiyl, more preferably, $(C_1-C_{10})$ alkyldiyl, most preferably, $(C_1-C_6)$ alkyldiyl. Preferred are saturated acyclic alkanyldiyl groups in which the radical centers are at the terminal carbons, e.g., methandiyl(methano); ethan-1,2-diyl (ethano); propan-1,3-diyl(propano); butan-1,4-diyl(butano); and the like (also referred to as alkyleno, defined infra).

"Alkyleno" by itself or as part of another substituent, refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. Preferably, the alkyleno group is $(C_1-C_{20})$ alkyleno, more preferably, $(C_1-C_{10})$ alkyleno, most preferably, $(C_1-C_6)$ alkyleno. Preferred are straight-chain saturated alkano groups, e.g., methano, ethano, propano, butano, and the like.

"Alkylsulfonyloxy" by itself or as part of another substituent, refers to a radical —$OS(O)_2R^{30}$ where $R^{30}$ represents an alkyl or cycloalkyl group as defined herein.

"Alkoxy" by itself or as part of another substituent, refers to a radical —$OR^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent, refers to a radical —$C(O)OR^{32}$ where $R^{32}$ represents an alkyl or cycloalkyl group as defined herein.

"Aryl" by itself or as part of another substituent, refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 5 to 20 carbon atoms, more preferably from 5 to 12 carbon atoms.

"Aryldiyl" by itself or as part of another substituent refers to a divalent hydrocarbon radical derived by the removal of one hydrogen atom from each of two different carbon atoms of a parent aromatic system or by removal of two hydrogen atoms from a single carbon atom of a parent aromatic ring system. The two monovalent radical centers or each valency of the divalent center can form bonds with the same or different atom(s). Typical aryldiyl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryldiyl group comprises from 5 to 20 carbon atoms, more preferably from 5 to 12 carbon atoms.

"Aryloxycarbonyl" by itself or as part of another substituent, refers to a radical —$C(O)OR^{33}$ where $R^{33}$ represents an aryl group as defined herein.

"Arylsulfonyloxy" by itself or as part of another substituent, refers to a radical —$OS(O)_2R^{35}$ where $R^{35}$ represents an alkyl or cycloalkyl group as defined herein.

"Cycloalkyl" by itself or as part of another substituent, refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. Preferably, the cycloalkyl group is ($C_3$-$C_{10}$) cycloalkyl, more preferably ($C_3$-$C_7$) cycloalkyl.

"Heteroalkyl, Heteroalkanyl, Heteroalkenyl, Heteroalkanyl, Heteroalkyldiyl and Heteroalkyleno" by themselves or as part of another substituent, refer to alkyl, alkanyl, alkenyl, alkynyl, alkyldiyl and alkyleno groups, respectively, in which one or more of the carbon atoms (and any associated hydrogen atoms) are each independently replaced with the same or different heteroatomic groups. Typical heteroatomic groups which can be included in these groups include, but are not limited to, —O—, —S—, —O—O—, —S—S—, —O—S—, —NR$^{35}$R$^{36}$—, =N—N=, —N=N—, —N=N—NR$^{37}$R$^{38}$, —PR$^{39}$—, —P(O)$_2$—, —POR$^{40}$—, —O—P(O)$_2$—, —SO—, —SO$_2$—, —S$_n$R$^{41}$R$^{42}$— and the like, where R$^{35}$, R$^{36}$, R$^{37}$, R$^{38}$, R$^{39}$, R$^{40}$, R$^{41}$ and R$^{42}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Preferred heteroaryl groups are those derived from thiophene, pyrrole, benzothiophene, benzofuran, indole, pyridine, quinoline, imidazole, oxazole and pyrazine.

"Heteroaryldiyl" by itself or as part of another substituent refers to a divalent radical derived by the removal of one hydrogen atom from each of two different carbon atoms of a parent heteroaromatic system or by removal of two hydrogen atoms from a single carbon atom of a parent aromatic ring system. The two monovalent radical centers or each valency of the divalent center can form bonds with the same or different atom(s). Typical heteroaryldiyl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, a heteroaryldiyl group comprises from 5 to 20 carbon atoms, more preferably from 5 to 12 carbon atoms.

"Parent Aromatic Ring System" by itself or as part of another substituent, refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" by itself or as part of another substituent, refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, "Substituted" refers to a group in which one or more hydrogen atoms are independently replaced with the same or different substituent(s). Typical substituents include, but are not limited to, -M, —R$^{60}$, —O$^-$, =OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O$_2$)O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is independently a halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring. Preferably, substituents include -M, —R$^{60}$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$R$^{60}$, —OS(O$_2$)O$^-$, —OS(O)$_2$R$^{60}$, —P(O)(O$^-$)$_2$, —P(O)(OR$^{60}$)

(O), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O, —NR$^{62}$C(O) NR$^{60}$R$^{61}$, more preferably, -M, —R$^{60}$, =O, —OR$^{60}$, —SR$^{60}$, —NR$^{60}$R$^{61}$, —CF$_3$, —CN, —NO$_2$, —S(O)$_2$R$^{60}$, —P(O)(OR$^{60}$)(O$^-$), —OP(O)(OR$^{60}$)(OR$^{61}$), —C(O)R$^{60}$, —C(O)OR$^{60}$, —C(O)NR$^{60}$R$^{61}$, —CF$_3$, —CN, —NO$_2$, —S(O)$_2$R$^{60}$, —OP(O)(OR$^{60}$)(OR$^{61}$, —C(O)R$^{60}$, —C(O) OR$^{60}$, —C(O)O$^-$, where R$^{60}$, R$^{61}$ and R$^{62}$ are as defined above.

6.2 Organosilanes and Substrates Thereof

The present invention provides novel silane compounds which have both hydrophobic and ionic functionality. At one terminus of the novel silane compound is a silyl group, which can be covalently attached to a substrate. At the other end of the novel silane compound is one or more ionic or ionizable groups which are optionally masked. The silyl group and the optionally masked ionic functionalities are connected via two linkers joined by a polar group. The linkers may be alkyl, aryl, heteroaryl or heteroalkyl groups while the polar group may be amide, carbamate, urea, oxygen, sulfur etc.

In one aspect, the present invention provides a compound described by Formula (I):

In some embodiments, compounds of Formula (I) are described by Formula (II):

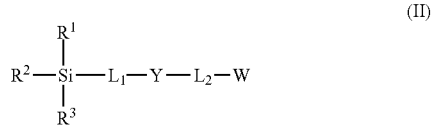

(II)

or salts, solvates or hydrates thereof
wherein:
R$^1$, R$^2$ and R$^3$ are independently alkyl, alkoxy, alkoxycarbonyl, alkylsulfortyloxy, amino optionally substituted with one or more of the same or different R$^{12}$ groups, aryl, aryloxycarbonyl, aryloxy, arylsulfonyloxy, halo or hydroxyl provided that at least one of R$^1$, R$^2$ and R$^3$ are not alkyl, aryl or hydroxyl;

L$_1$ and L$_2$ are independently alkyldiyl, heteroalkyldiyl, aryldiyl or heteroaryldiyl;

Y is —S—, —O—, —C(O)N(R$^4$)—, —N(R$^4$)C(O)—, —N(R$^4$)S(O)$_2$—, —S(O)$_2$N(R$^4$)—, —C(O)O—, —OC(O)—, —OC(O)N(R$^4$)—, —N(R$^4$)C(O)O—, —N(R$^4$)C(O)N(R$^5$)— or —N(R$^4$)C(S)N(R$^5$)—;

R$^4$ and R$^5$ are independently hydrogen, alkyl, substituted alkyl, aryl or substituted aryl;

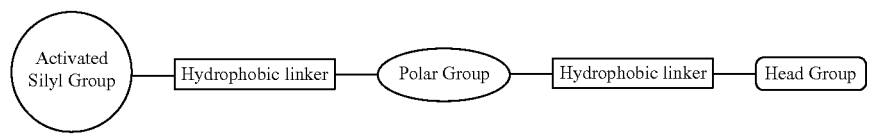

(I)

or salts, solvates or hydrates thereof. Compounds of Formula (I) have at least one activated silyl group and at least one head group and at least one polar group between the activated silyl group and the head group. The head group contains one or more ion-exchange functionalities which are optionally masked. The compound of Formula (I) also contain two alkyl, aryl, heteroalkyl or heteroaryl linkers which connect the activated silyl group with the polar group and the polar group with a head group as illustrated, supra.

An "activated silyl group" refers to silicon moieties, which are capable of reacting with the surface of a substrate to form a covalent bond with the surface. For example, an activated silyl group can react with the surface of a silica substrate comprising surface Si—OH groups to create siloxane bonds between compounds of Formula (I) and the substrate. Exemplary activated silyl groups include, but are not limited to, —Si(OMe)$_3$, —SiMe(OMe)$_2$, —SiMe$_2$(OMe), —Si(OEt)$_3$, —SiMe(OEt)$_2$, —SiMe$_2$(OEt), —SiMe$_2$NMe$_2$ and —SiCl$_3$.

An "ion-exchange functionality" refers to a moiety containing one or more ion-exchange groups. Examples of ion exchange functionalities include, but are not limited to, primary amines, secondary amines, tertiary amines, quaternary amines, phenols, carboxylic acids, sulfonic acids and phosphonic acids. Typically, a head group contains one or more ion-exchange functionalities. Additionally, a head group may contain moieties that can be converted into ion-exchange functionalities such as, for example, esters of phenols, carboxylic acids, sulfonic acids and phosphonic acids.

A "linker" refers to an alkyl, heteroalkyl, aryl or heteroaryl group. The linkers in compounds of Formula (I) are connected by a polar group such as, for example, an amide, sulfonamide, carbamate, urea, ester, ether or thioether.

W is —(Z)$_n$OH, —(Z)$_n$N(R$^6$)(R$^7$), —(Z)$_n$N$^+$(R$^6$)(R$^7$)(R$^8$) X$^-$—, —(Z)$_n$CO$_2$R$^9$,
—(Z)$_n$SO$_3$R$^9$, or —(Z)$_n$OP(O)(OR$^9$)(OR$^{10}$) or —(Z)$_n$B(OR$^9$)(OR$^{10}$)(OR$^{11}$);

R$^6$, R$^7$ and R$^8$ are independently hydrogen, alkyl or substituted alkyl;

R$^9$, R$^{10}$ and R$^{11}$ are independently hydrogen, alkyl, substituted alkyl, aryl or substituted aryl;

R$^{12}$ is hydrogen or alkyl;

X$^-$ is an anionic counterion;

Z is aryl or substituted aryl; and n is 0 or 1 provided that when W is —(Z)$_n$OH, n is 1.

In some embodiments, R$^1$, R$^2$ and R$^3$ are independently alkyl, alkoxy, halo or amino optionally substituted with one or more R$^2$ groups. In other embodiments, R$^1$, R$^2$ and R$^3$ are independently alkyl, alkoxy or halo.

In still other embodiments, L$_1$ and L$_2$ are independently alkyldiyl or aryldiyl. In some embodiments, L$_1$ and L$_2$ are alkanyldiyl. In other embodiments, L$_1$ and L$_2$ are alkyleno. In still other embodiments, Li is (C$_4$-C$_{30}$) alkanyleno, (C$_4$-C$_{20}$) alkanyleno or (C$_1$-C$_{10}$) alkanyleno. In still other embodiments, L$_2$ is (C$_1$-C$_{30}$) alkanyleno, (C$_1$-C$_{20}$) alkanyleno, (C$_1$-C$_{10}$) alkanyleno or phenyldiyl. In still other embodiments, L$_1$ is (C$_4$-C$_{18}$) alkanyleno. In still other embodiments, (C$_1$-C$_{30}$) alkanyleno L$_2$ is (C$_1$-C$_{18}$) alkanyleno.

In still other embodiments, L$_1$ is (C$_4$-C$_{30}$) alkanyleno, (C$_4$-C$_{20}$) alkanyleno or (C$_4$-C$_{10}$) alkanyleno and L$_2$ is (C$_1$-C$_{30}$) alkanyleno, (C$_1$-C$_{20}$) alkanyleno, (C$_1$-C$_{10}$) alkanyleno or phenyldiyl. In still other embodiments, L$_1$ is (C$_4$-C$_{30}$) alkanyleno and L$_2$ is (C$_1$-C$_{30}$) alkanyleno or phenyldiyl. In still other embodiments, L$_1$ is (C$_4$-C$_{12}$) alkanyleno and L$_2$ is (C$_1$-C$_8$) alkanyleno or phenyldiyl.

In some embodiments, Y is —C(O)N(R$^4$)—, —N(R$^4$)C(O)—, —N(R$^4$)S(O)$_2$—, —S(O)$_2$N(R$^4$)—, —C(O)O—, —OC(O)—, —OC(O)N($R^4$)— or —N($R^4$)C(O)O—. Preferably, $R^4$ and $R^5$ are independently hydrogen, alkyl or substituted alkyl, more preferably, hydrogen or alkyl.

In other embodiments, W is —N($R^6$)($R^7$) or —N$^+$($R^6$)($R^7$)($R^8$)X$^-$—. Preferably, $R^6$, $R^7$ and $R^8$ are independently hydrogen or alkyl. In still other embodiments, W is —(Z)$_n$OH, —CO$_2$R$^9$, —SO$_3$R$^9$ or —OP(O)(OR$^9$)(OR$^{10}$). Preferably, $R^9$, $R^{10}$ and $R^{11}$ are independently hydrogen, alkyl or substituted alkyl, more preferably, hydrogen or alkyl.

In some embodiments, $R^1$, $R^2$ and $R^3$ are independently alkyl, alkoxy or halo, $L^1$ is (C$_4$-C$_{30}$) alkanyldiyl, $L^2$ is (C$^1$-C$^{30}$) alkanyldiyl, $R^4$ and $R^5$ are hydrogen or alkyl, $R^6$ and $R^7$ are independently hydrogen or alkyl optionally substituted with one or amino groups, $R^8$ is hydrogen or alkyl, optionally substituted with one or more —OH, —CN, aryl or perfluoro groups, W is —(Z)$_n$N($R^6$)($R^7$) or —(Z)$_n$N$^+$($R^6$)($R^7$)($R^8$)X$^-$ and $R^6$, $R^7$ and $R^8$ are independently hydrogen or alkyl. In some of these embodiments, $R^1$, $R^2$ and $R^3$ are —CH$_3$ or —OC$_2$H$_5$. In other of these embodiments, $R^2$ is —OC$_2$H$_5$ and $R^1$ and $R^3$ are —CH$_3$. In still other of these embodiments, $L_1$ is (C$_4$-C$_{18}$) alkanyldiyl and $L_2$ is (C$_1$-C$_{18}$) alkanyldiyl. In still other of these embodiments, $L_1$ is (C$_8$-C$_{12}$) alkanyidiyl. In still other of these embodiments, Y is —C(O)N($R^4$)— and $R^4$ is hydrogen. In still other of these embodiments, $L_2$ is (C$_1$-C$_5$) alkanyldiyl or phenyldiyl. In still other of these embodiments, W is —N($R^6$)($R^7$), or —N$^+$($R^6$)($R^7$)($R^8$)X$^-$.

Exemplary compounds encompassed by the above embodiments include

1

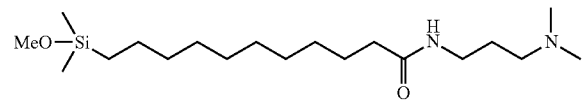

and

2

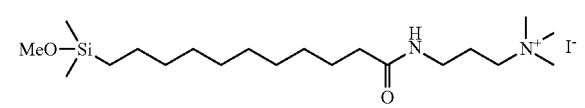

In some other embodiments, $R^1$, $R^2$ and $R^3$ are independently alkyl, alkoxy or halo, $L_1$ is (C$_4$-C$_{30}$) alkanyldiyl, $L_2$ is (C$_1$-C$_{30}$) alkanyldiyl or aryldiyl, Y is —S—, —O—, —C(O)N($R^4$)—, —N($R^4$)C(O)—, —N($R^4$)S(O)$_2$—, —S(O)2N(R4)-, —C(O)O—, —OC(O)—, —OC(O)N($R^4$)—, —N($R^4$)C(O)O—, or —N($R^4$)C(O)N($R^5$)—, $R^4$ and $R^5$ are hydrogen or alkyl, W is —(Z)$_n$OH, —(Z)$_n$CO$_2$R$^9$, —(Z)$_n$SO$_3$R$^9$ or —(Z)$_n$OP(O)(OR$^9$)(OR$^{10}$) and $R^9$ and $R^{10}$ are independently hydrogen or alkyl, in some of these embodiments, $L_1$ is (C$_4$-C$_{18}$) alkanyldiyl and $L_2$ is (C$_1$-C$_{18}$) alkanyldiyl. In other of these embodiments, $R^1$, $R^2$ and $R^3$ are —C$_{1-13}$ or —OC$_2$H$_5$. In still other of these embodiments, $R_2$ is —OC$_2$H$_5$ and $R^1$ and $R^3$ are —C$_1$H$_3$. In still other of these embodiments, $L_1$ is (C$_8$-C$_{12}$) alkanyldiyl. In still other of these embodiments, Y is —C(O)N($R^4$)— and $R^4$ is hydrogen. In still other of these embodiments, $L_2$ is (C$_1$-C$_5$) alkanyldiyl or phenyldiyl. In still other of these embodiments, W is —CO$_2$R$^9$ or —SO$_3$R$^9$.

Exemplary compounds encompassed by the above embodiments include

3

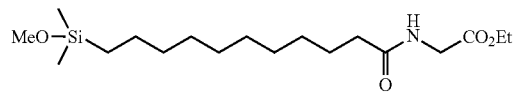

4

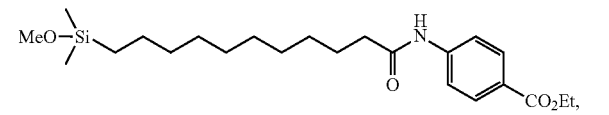

5

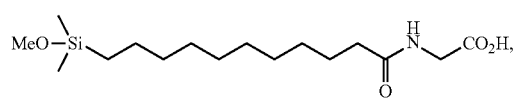

6

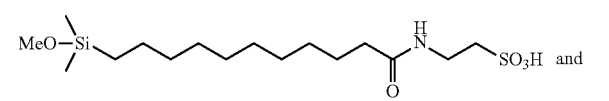

7

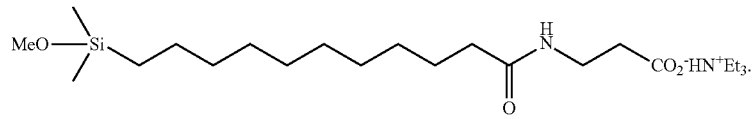

Exemplary methods of synthesizing compounds described herein are presented in Schemes 1-3, infra. Starting materials useful for preparing compounds described herein are commercially available or can be prepared by well-known synthetic methods. Other methods for synthesis of the compounds described herein will be readily apparent to the skilled artisan. Accordingly, the methods presented in Schemes 1-3 herein are illustrative rather than comprehensive.

Referring now to Scheme 1, infra, amine 8 with at least one primary or secondary amino group is reacted with acyl chloride 9 which contains a terminal double bond. The resulting compound 10 is then hydrosilylated with silane 11 in presence of a platinum catalyst to provide compound 12. Compound 12 may be converted into compound 13 by reaction with an alkyl halide or an epoxide.

Scheme 1

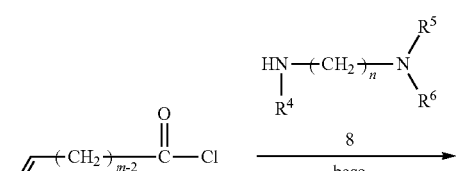

-continued

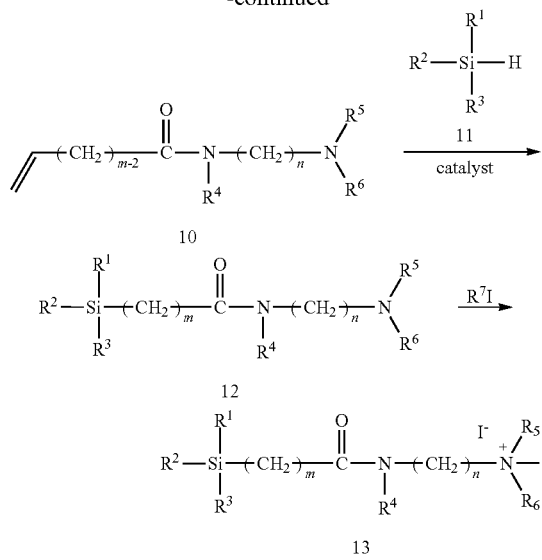

m = 4 to 30

Referring now to Scheme 2, infra, compound 14 containing at least one primary or secondary amino group and at least one free or protected (see, e.g., Green et al., "Protective Groups in Organic Chemistry", (Wiley, 2$^{nd}$ ed. 1991) carboxylic acid, sulfonic acid or phosphonic acid functionality is reacted with an acyl chloride 9 containing a terminal double bond. The resulting compound 15 is then hydrosilylated with silane 11 in the presence of a platinum catalyst to provide compound 16.

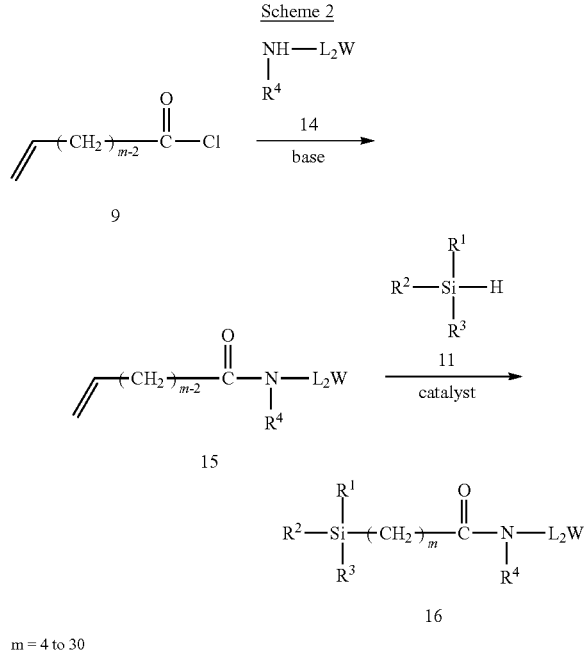

m = 4 to 30

Referring now to Scheme 3, infra, primary amine 17 is allowed to react with the halide 18 containing a terminal double bond to provide compound 19, which is then hydrosilylated with silane 11 in the presence of a platinum catalyst to provide compound 20. Reaction of compound 20 with anhydride 21 provides compound 21.

Scheme 3

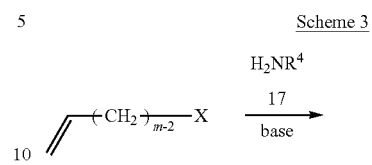

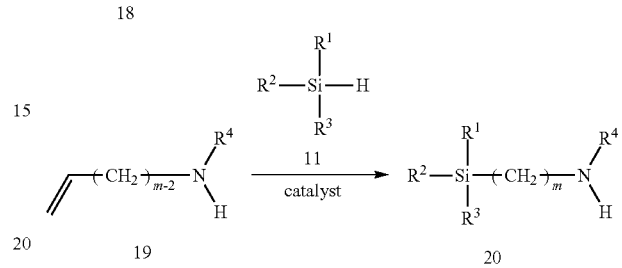

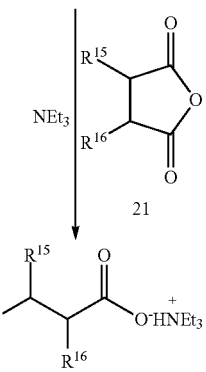

M = 4 to 30, R$^{15}$ and R$^{16}$ are hydrogen, alkyl substituted alkyl

Those of skill in the art will appreciate that the synthetic strategies disclosed, supra, may be readily adapted to make silanes with aryl, heteroaryl and heteroalkyl linkers by varying the starting amine or acyl chloride or alkyl halide. Further, diverse methods are known to those of skill in the art to accomplish the transformations above (or equivalents thereof) and may be found in any compendia of organic synthesis (see e.g., Harrison et al., "Compendium of Synthetic Organic Methods", Vols, 1-8 (John Wiley and Sons, 1971-1996); "Beilstein Handbook of Organic Chemistry," Beilstein Institute of Organic Chemistry, Frankfurt, Germany; Feiser et al, "Reagents for Organic Synthesis," Volumes 1-17, Wiley Interscience; Trost et al., "Comprehensive Organic Synthesis," Pergamon Press, 1991 "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; and Paquette, "Encyclopedia of Reagents for Organic Synthesis," John Wiley & Sons, 1995).

The compounds disclosed, supra, may be reacted with substrates to form functionalized substrates, which can be used in a wide range of different applications. The compounds disclosed, supra, incorporate both hydrophobic and ion-exchange sites in one molecular structure and have reproducible surface chemistries in reactions with substrate surfaces.

In some embodiments, compounds of Formulae (I) and (II) are covalently attached to substrates. In these embodiments, the ionizable group is disposed relatively far from the surface of the substrate, which may improve hydrolytic stability of the functionalized substrate. Compounds of Formulae (I) and (II) can be attached to substrates (e.g., substrates) to provide a functionalized stationary phase for various chromatographic separations particularly, reversed phase separations. The resulting material can be regarded as a mixed-mode substrate. As used herein "mixed mode substrate" refers a substrate modified with compounds with both hydrophobic and ionic moieties, which can retain organic molecules by hydrophobic interaction, ion exchange interaction or hydrogen bonding interaction or combinations thereof. Accordingly, mixed mode substrates provide flexibility in resolving ionic and neutral analytes present in the same sample. For example, ionic compounds and neutral molecules can be separated in the same chromatographic run by applying either hydrophobic or ion-exchange retention mechanisms, which can be selected through manipulation of experimental variables. Further, compounds of Formulae (I) and (II) may be mixed with conventional C1, C8, phenyl or C18 silyl ligands as well as polar embedded ligands prior to substrate functionalization to provide mixed mode substrates of varying selectivity.

Compounds of Formulae (I) and (II) may be covalently bound to a substrate by reaction of R, R2 or R3 of the Si functionality with reactive groups on the substrate selected from the group consisting of silanol, alkoxysilane, halosilane and aminosilane moieties. In some embodiments, compounds of Formulae (I) and (I) which are covalently bonded to a substrate may be cross linked to one or more compounds of Formulae (I) and (II) by reaction with reactive groups selected from the group consisting of silanol, alkoxysilane or halosilane on the other compound of Formulae (I) and (II).

Compounds of Formulae (I) and (II) can be covalently attached to a variety of substrates. Exemplary substrates include materials that have a functional group that can react with activated silyl groups in compounds of Formulae (I) and (II). Thus, compounds of Formulae (I) and (II) can be attached, for example, to silica based materials such as glass surfaces, or the surfaces of other silicon oxide, titanium oxide, germanium oxide, zirconium oxide and aluminum oxide based materials; and also to the surfaces of various carbonized materials, metals, crosslinked and non-crosslinked polymers, which contain suitable functional groups for reacting with the activated silyl groups. Examples of suitable functional groups include silanols, alkoxysilanes, titanium hydroxides, zirconium hydroxides, etc. Compounds of Formulae (I) and (II) cart also be incorporated into polymeric or sol-gel networks by utilizing reactive silicon functionalities. Compounds of Formulae (I) and (II) containing polymerizable groups or groups that can be converted into radicals and/or ion-radicals and/or ions, can be used for making polymeric materials and for surface grafting, by utilizing those groups and/or reactive silicon functionalities. The resulting materials can be applied for a development of adsorbents, membranes, filters, microfluidic devices, microchips, and functionalized surfaces for various types of separation, detection, and analysis.

In some embodiments, a composition of structural Formula (III) is provided:

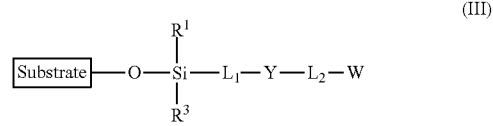

wherein $R^1$, $R^3$, $L_i$, $L_2$, Y and W are as defined, supra. Those of skill in the art will appreciate that embodiments of compounds of Formula (II) are also embodiments of compositions of Formula (III). Some exemplary compositions are shown below.

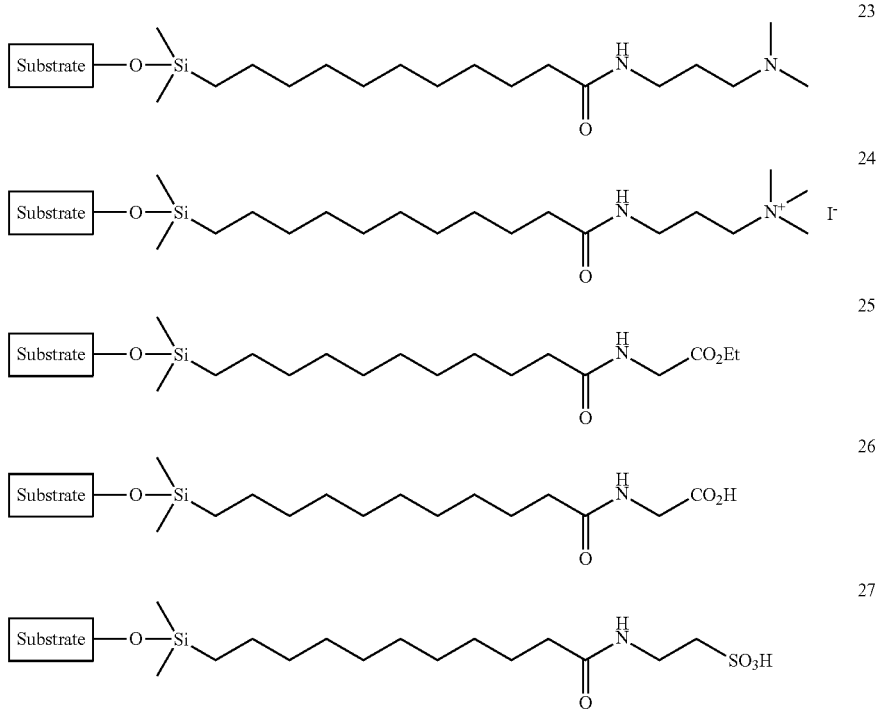

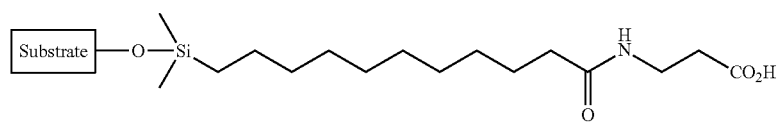

28

In some embodiments, mono- and multi-layered surfaces are prepared by treating silica substrates with compounds of Formulae (I) and (II). Compounds of Formulae (I) and (II) can be covalently attached to a variety of substrates, such as silica gel, zirconia, hybrid sol-gel/polymers or glass plates. Suitable silica, gels comprise non-porous, or porous silica particles of different pore sizes, preferably from 20 Å to 3000 Å and more preferably, from 60 Å to 2000 Å; and of different particle sizes, preferably, from 0.2 um to 1000 um, and more preferably, from 2 um to 50 um. The attachment reaction can be carried out in a slurry of silica gel in an inert solvent, such as toluene, at elevated temperature. Water, acid or base catalyst can be applied to enhance the surface coverage, depending on the type of properties desired for the separation media.

Alternatively, an aminosilane compound, such as bis(trimethoxysilylpropyl)amine can be used for modifying underivatized silica gel by incorporating the reactive amino group onto a surface. Then, a reagent, such as acyl chloride, carbamyl chloride, sulfonyl chloride, or isocyanate, containing a proper functional group, can be reacted with the aminated silica gel to form the corresponding bonded phase.

This invention provides simple and versatile approaches to produce a variety of novel solid supports with excellent hydrolytic stability. The method of synthesis allows for efficient incorporation of different functionalities onto the surfaces of the substrates and silica substrates, in particular. The resulting materials can be applied for development of adsorbents, membranes, filters, microfluidic devices, microchips, and functionalized surfaces for various types of separation, detection and analysis.

7. EXAMPLES

The following examples are provided by way of illustration only and not by way of limitation. Those of skill in the art will readily recognize a variety of noncritical parameters that could be changed or modified to yield essentially similar results.

7.1 Preparation of Compound 1

(Dimethylanamino)propylamine was mixed with an excess of triethylamine (2.0 equiv.) in anhydrous $CH_2Cl_2$ and kept at between about 0° C. to about 5° C. for 20 min. Then, a solution of 10-undecenoyl chloride (1.0 equiv) in $CH_2C_{12}$ was added dropwise and the mixture was stirred at ambient temperature for 12 h. The reaction mixture was washed with water, dried over $Na_2SO_4$ and the solvent was removed in vacuo to yield the dimethylaminopropylamide of 10-undecenoic acid. Excess dimethyl ethoxysilane (10 equiv) was added to the amide followed by addition of a solution of catalyst (0.1 mol %), (e.g., hexachloroplatinic acid in a minimum amount of ethanol). After stirring at 50° C. for 24 h, the silane and solvent were removed in vacuo to provide silyl compound 1.

7.2 Example 2

Preparation of Compound 2

To a solution of 1 (1 equiv.) in acetonitrile, a solution of iodomethane (1.1 equiv) in acetonitrile was added dropwise at room temperature. The reaction mixture was stirred at ambient temperature for 24 hours. After removal of all volatiles in vacuo, compound 2 was obtained in quantitative yield.

7.3 Example 3

Preparation of Compound 3

Glycine ethyl ester hydrochloride was mixed with an excess of triethylamine (4.0 equiv.) in $CH_2Cl_2$ and was kept at between 0° C.-5° C. for 20 mM. A solution of 10-undecenoyl chloride (1.0 equiv) in $CH_2C_{12}$ was added dropwise and the reaction mixture was stirred at ambient temperature for 12 hours. The reaction mixture was washed with water and dried over $Na_2SO_4$ and volatiles removed in vacuo to provide the glycine amide of 10-undenoic acid. The amide was hydrosilated by addition of excess dimethylethoxysilane (10 equiv) and a solution of catalyst (0.1 mol %), (e.g., hexachloroplatinic acid in a minimum amount of ethanol). After stirring at 50° C. for 24 hours, the silane and solvent were removed in vacuo to yield compound 3.

7.4 Example 4

Synthesis of Compositions 23, 25 and 26

Compound 1 or 3 in an inert solvent such as toluene at elevated temperature was mixed with a slurry of selected raw silica gel with the following physical properties: average particle size, 5.0 µm; specific surface area, 300 $m^2$/g; mean pore size, 120 Å; pore volume, 1.00 mL/g. The addition of water, acid or base catalyst can be applied to control the surface coverage. A proper end-capping reagent, such as a trialkylsilyl chloride, may also be required to produce a packing material for the reversed-phase chromatographic separation. The final step in the synthesis of composition 26 is hydrolysis of the terminal ester group under acidic conditions (e.g., a solution of 10 mmol methane sulfonic acid is passed over packed silica beads at 1 mml/min for 24 hours at room temperature).

7.5 Example 5

Synthesis of Composition 24

To a slurry of composition 23 in acetonitrile, an excess of iodomethane (1/1 by weight of silica) was added. The reaction mixture was stirred at ambient temperature for 24 hours. After filtering, the composition was washed with acetonitrile, ether and dried to yield composition 24.

7.6 Example 6

Mixed Mode Evaluation Test

HPLC chromatography of a test mixture containing a neutral compound (toluene), a basic compound (α-methylbenzylamine) and two acidic compounds (fumaric acid and p-butylbenzoic acid) on composition 23 packed into 4.6×150 mm stainless steel tubes using traditional high pressure slurry techniques yielded the results illustrated in FIG. 1. The mixture was eluted with, $CH_3CN/20$ mM $Na_2SO_4$ (50:50 v/v) at different pHs (adjusted with methanesulfonic acid) at a flow rate of 1 mL/min; injection volume of 5 μL; temperature of 30° C.; and detection at 210 nm.

FIG. 1 illustrates the mix-mode character of the composition 23, since a neutral analyte (i.e., toluene) is retained along with acidic compounds (i.e., fumaric acid and p-butylbenzoic acid). No retention is observed for basic analyte (i.e., α-methylbenzylamine). The retention time of p-butylbenzoic acid is longer than the retention time of fumaric acid, presumably due to the greater hydrophobicity of the aromatic acid. Fumaric acid and p-butylbenzoic acid have greater retention times at higher pH (i.e., 3.6) than at lower pH (i.e., 3.0), presumably, because of the greater percentage of the ionized carboxylate form at higher pH. Moreover, the increase in retention time for fumaric acid and p-butylbenzoic acid occurs without any retention time change for the neutral analyte (i.e., toluene). The selectivity of composition 23 can be modified by changing the ionic strength and composition of the mobile phase.

7.7 Example 7

Separation of Common Hydrophilic Monocarboxylic Acids

Figure 2:
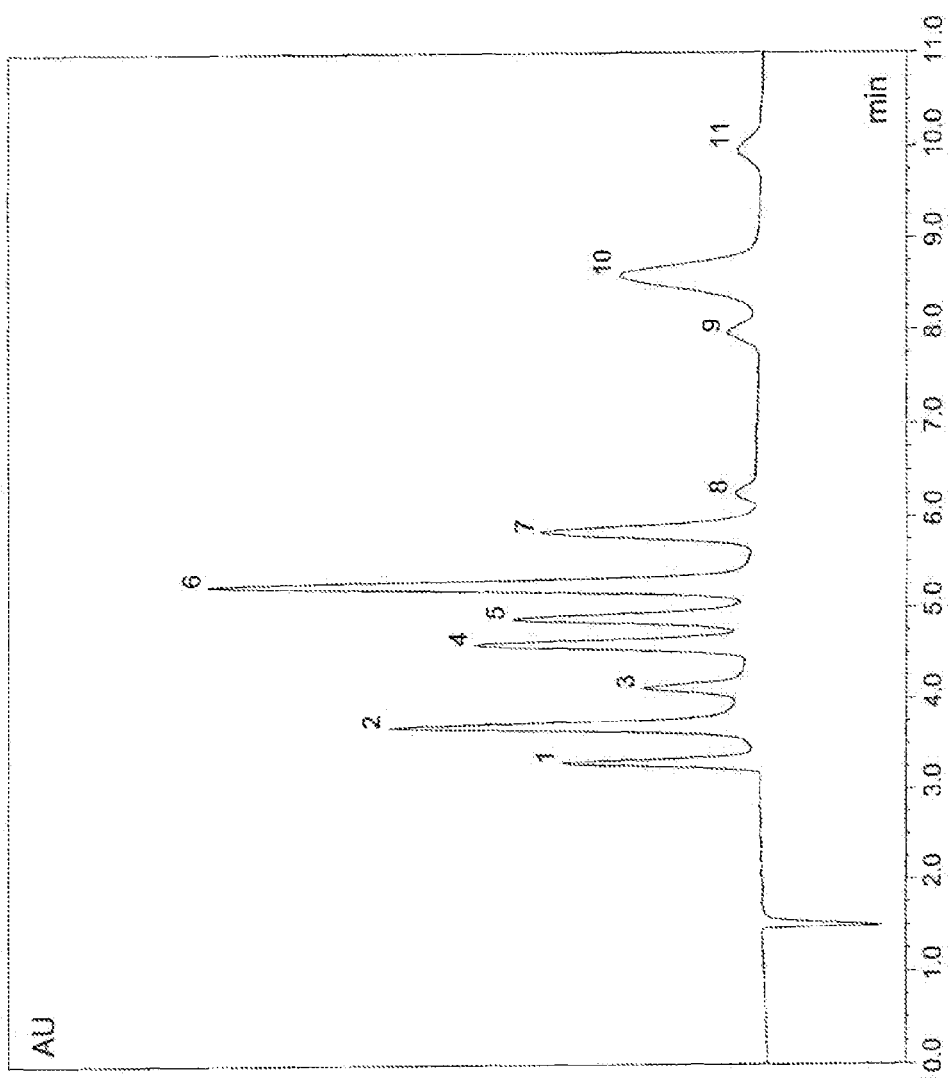
FIG. 2 illustrates separation of 10 hydrophilic carboxylic acids with support 23.

HPLC chromatography of a test mixture containing 10 common hydrophilic monocarboxylic acids on composition 23 packed into 4.6×150 mm stainless steel tubes using traditional high pressure slurry techniques yielded the results illustrated in FIG. 2. The test mixture was eluted with 25 mM $K_2HPO_4/KH_2PO_4$, pH 6.0; flow rate of 1 mL/min; injection volume of 10 μL; temperature of 30° C.; and detection at 210 nm.

7.8 Example 8

Dewetting Test

Figure 3:
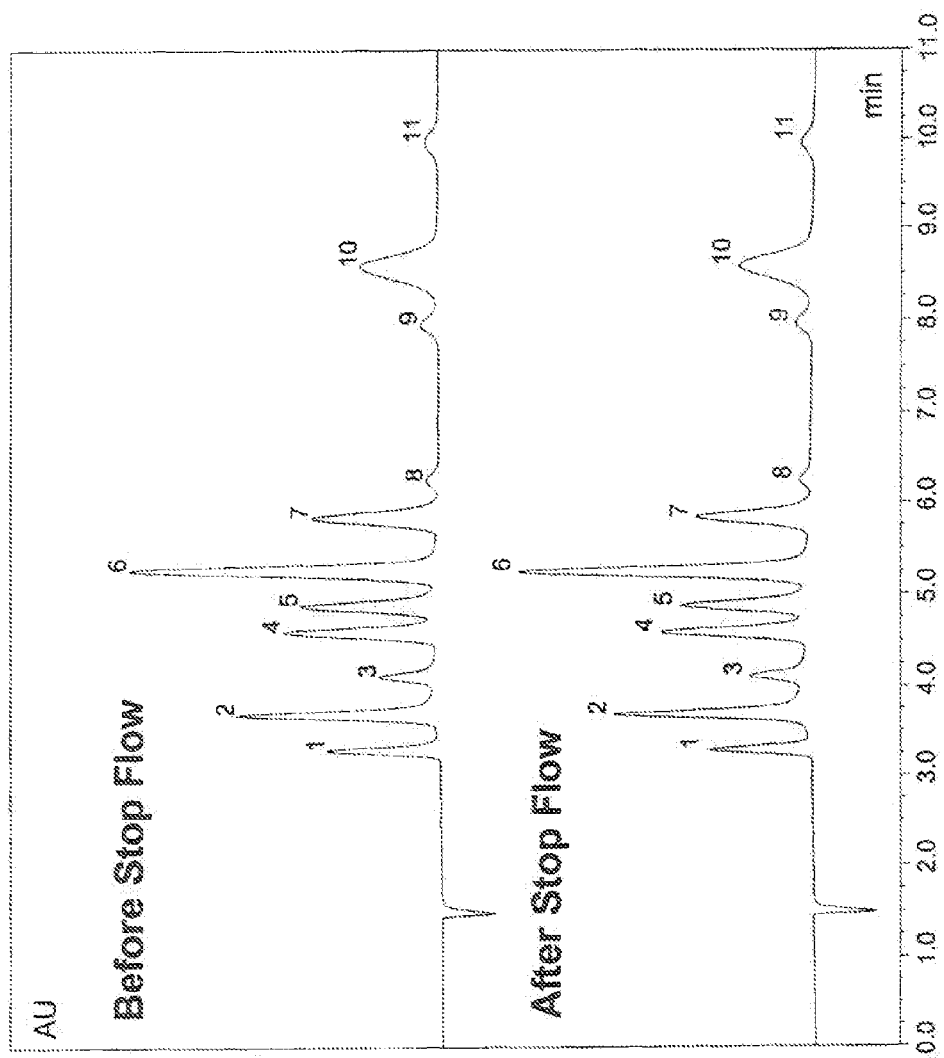
FIG. 3 illustrates the performance of support 23 before stop flow and after stop flow in a 100% aqueous environment.

Composition 23 was tested in 25 mM $K_2HPO_4/KH_2PO_4$, pH 6 mobile phase at 30° C. A freshly packed column contain composition 23 was washed with 50 column volumes of $CH_3CN$, and equilibrated with 50 column volumes of the mobile phase. The sample solution contained 10 common hydrophilic monocarboxylic acids shown in FIG. 3. In the stop-flow test, each test cycle consisted of two steps. In the first step the column is equilibrated with a mobile phase for 20 minutes. A sample is injected and the data acquired during 10 minutes. In the second step, flow was stopped for 30 min before initiating the next cycle. Fifty cycles were performed. Other testing conditions: flow rate of 1 mL/min; injection volume of 10 μL; detection at 210 nm. This test demonstrates that composition 23 provided consistent retention and good peak efficiency in 100% aqueous media.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications and patent documents cited in this specification are herein incorporated by reference in their entirety.

What is claimed is:

1. A chromatographic method comprising flowing an aqueous liquid through a bed of separation medium comprising a composition comprising a substrate, wherein the substrate comprises a compound covalently bound to said substrate, said compound having a structure according to Formula (II):

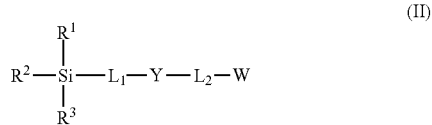

or a salt, solvate or hydrate thereof,
wherein
$R^1$, $R^2$ and $R^3$ are independently alkyl, alkoxy, alkoxycarbonyl, alkylsulfonyloxy, amino optionally substituted with one or more of the same or different alkyl groups, aryl, aryloxycarbonyl, aryloxy, arylsulfonyloxy, halo or hydroxyl provided that at least one of $R^1$, $R^2$ and $R^3$ is covalently bound to said substrate;
$L_1$ is at least $C_8$ alkanyldiyl;
$L_2$ is alkyldiyl or aryldiyl;
Y is —C(O)N($R^4$)—, —N($R^4$)S(O)$_2$—, —S(O)$_2$N($R^4$)—, —C(O)O—, —OC(O)—, —OC(O)N($R^4$)—, —N($R^4$)C(O)O—, —N($R^4$)C(O)N($R^5$)— or —N($R^4$)C(S)N ($R^5$)—, wherein $R^4$ and $R^5$ are independently hydrogen, alkyl, substituted alkyl, aryl or substituted aryl; and
W is —(Z)$_n$CO$_2$R$^9$ or —(Z)$_n$SO$_3$R$^9$,
wherein
$R^9$ is hydrogen, alkyl, substituted alkyl, aryl or substituted aryl;
Z is aryl or substituted aryl; and
n is 0 or 1.

2. A method for the chromatographic separation of analytes in a liquid sample comprising flowing the liquid sample through a medium comprising a composition comprising a substrate, wherein the substrate comprises a compound covalently bound to said substrate, said compound having a structure according to Formula (II):

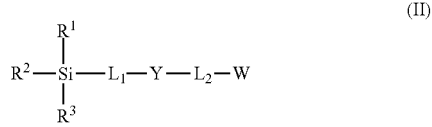

or a salt, solvate or hydrate thereof,
wherein
$R^1$, $R^2$ and $R^3$ are independently alkyl, alkoxy, alkoxycarbonyl, alkylsulfonyloxy, amino optionally substituted with one or more of the same or different alkyl groups, aryl, aryloxycarbonyl, aryloxy, arylsulfonyloxy, halo or hydroxyl provided that at least one of $R^1$, $R^2$ and $R^3$ is covalently bound to said substrate;
$L_1$ is at least $C_8$ alkanyldiyl;
$L_2$ is alkyldiyl or aryldiyl;
Y is —C(O)N($R^4$)—, —N($R^4$)S(O)$_2$—, —S(O)$_2$N($R^4$)—, —C(O)O—, —OC(O)—, —OC(O)N($R^4$)—, —N($R^4$)C(O)O—, —N($R^4$)C(O)N($R^5$)— or —N($R^4$)C(S)N ($R^5$)—, wherein $R^4$ and $R^5$ are independently hydrogen, alkyl, substituted alkyl, aryl or substituted aryl; and W is —$(Z)_nCO_2R^9$ or —$(Z)_nSO_3R^9$, wherein
$R^9$ is hydrogen, alkyl, substituted alkyl, aryl or substituted aryl;
Z is aryl or substituted aryl; and
n is 0 or 1.

3. A method for simultaneous analysis of inorganic analytes and organic analytes in a liquid sample comprising flowing the liquid sample through a medium comprising a composition comprising a substrate, wherein the substrate comprises a compound covalently bound to said substrate, said compound having a structure according to Formula (II):

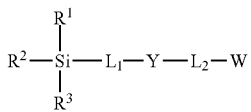

(II)

or a salt, solvate or hydrate thereof, wherein
$R^1$, $R^2$ and $R^3$ are independently alkyl, alkoxy, alkoxycarbonyl, alkylsulfonyloxy, amino optionally substituted with one or more of the same or different alkyl groups, aryl, aryloxycarbonyl, aryloxy, arylsulfonyloxy, halo or hydroxyl provided that at least one of $R^1$, $R^2$ and $R^3$ is covalently bound to said substrate;

$L_1$ is at least $C_8$ alkanyldiyl;

$L_2$ is alkyldiyl or aryldiyl;

Y is —$C(O)N(R^4)$—, —$N(R^4)S(O)_2$—, —$S(O)_2N(R^4)$—, —$C(O)O$—, —$OC(O)$—, —$OC(O)N(R^4)$—, —$N(R^4)C(O)O$—, —$N(R^4)C(O)N(R^5)$— or —$N(R^4)C(S)N(R^5)$—, wherein $R^4$ and $R^5$ are independently hydrogen, alkyl, substituted alkyl, aryl or substituted aryl; and W is —$(Z)_nCO_2R^9$ or —$(Z)_nSO_3R^9$, wherein
$R^9$ is hydrogen, alkyl, substituted alkyl, aryl or substituted aryl;
Z is aryl or substituted aryl; and
n is 0 or 1.

* * * * *

UNITED STATES PATENT AND TRADEMARK OFFICE
CERTIFICATE OF CORRECTION

PATENT NO. : 8,425,778 B2
APPLICATION NO. : 13/464644
DATED : April 23, 2013
INVENTOR(S) : Xiaodong Liu et al.

It is certified that error appears in the above-identified patent and that said Letters Patent is hereby corrected as shown below:

On the Title Page of the patent, in item (75) Inventors: Replace "Xiadong Liu" with --Xiaodong Liu--

Signed and Sealed this
Sixth Day of August, 2013

Teresa Stanek Rea
*Acting Director of the United States Patent and Trademark Office*